United States Patent
Rubin et al.

(10) Patent No.: US 10,733,771 B2
(45) Date of Patent: Aug. 4, 2020

(54) IMAGE RECONSTRUCTION WITH RADIOACTIVE IMAGING CAPSULE

(71) Applicant: CHECK-CAP LTD., Isfiya (IL)

(72) Inventors: Daniel Rubin, Haifa (IL); Ronen Lifshitz, D.N. Misgav (IL); Yoav Kimchy, Isfiya (IL)

(73) Assignee: CHECK-CAP LTD, Isfiya (IL)

( * ) Notice: Subject to any disclaimer, the term of this patent is extended or adjusted under 35 U.S.C. 154(b) by 119 days.

(21) Appl. No.: 16/311,690

(22) PCT Filed: Jul. 31, 2017

(86) PCT No.: PCT/IL2017/050848
§ 371 (c)(1),
(2) Date: Dec. 20, 2018

(87) PCT Pub. No.: WO2018/025262
PCT Pub. Date: Feb. 8, 2018

(65) Prior Publication Data
US 2019/0213760 A1 Jul. 11, 2019

Related U.S. Application Data

(60) Provisional application No. 62/369,217, filed on Aug. 1, 2016.

(51) Int. Cl.
*G06K 9/00* (2006.01)
*G06T 11/00* (2006.01)
(Continued)

(52) U.S. Cl.
CPC .............. *G06T 11/005* (2013.01); *A61B 5/07* (2013.01); *A61B 6/06* (2013.01); *A61B 6/4057* (2013.01);
(Continued)

(58) Field of Classification Search
None
See application file for complete search history.

(56) References Cited

U.S. PATENT DOCUMENTS

| 2007/0161885 A1 | 7/2007 | Kimchy |
| 2009/0110321 A1 | 4/2009 | Vija et al. |

(Continued)

OTHER PUBLICATIONS

Kimchy, Y., Lifshitz, R., Lewkowitz, S., Bertuccio, G., Arber, N., Gluck, N., and Pickhardt P. J., "Radiographic capsule-based system based system for non-cathartic colorectal cancer screening", Abdominal Radiology 2017.

(Continued)

*Primary Examiner* — Atiba O Fitzpatrick
(74) *Attorney, Agent, or Firm* — Soroker Agmon Nordman

(57) ABSTRACT

A method of reconstructing an image of a colon, including receiving scan data of a colon taken by an imaging capsule that traverses the colon; wherein the imaging capsule emits X-ray radiation inside the colon and includes detectors that detect photons that are returned toward the imaging capsule from X-ray fluorescence and Compton back scattering interactions responsive to the radiation; and wherein the scan data includes counts of photons detected by each detector from X-ray fluorescence and Compton back scattering interactions; defining an initial guess of a geometry of a contour of a slice of the colon; calculating count values for each detector responsive to the geometry using a forward model; comparing the calculated count values of each detector with the values from the scan data; if the results of the comparison do not indicate reaching an optimal match then adjust the defined geometry and repeat the calculating and comparing.

20 Claims, 10 Drawing Sheets

(51) Int. Cl.
*A61B 6/00* (2006.01)
*A61B 5/07* (2006.01)
*A61B 6/06* (2006.01)

(52) U.S. Cl.
CPC ............ *A61B 6/425* (2013.01); *A61B 6/4241* (2013.01); *A61B 6/4266* (2013.01); *A61B 6/483* (2013.01); *A61B 6/485* (2013.01); *A61B 6/50* (2013.01); *A61B 6/5205* (2013.01); *A61B 6/547* (2013.01); *A61B 6/56* (2013.01); *A61B 6/582* (2013.01); *A61B 6/481* (2013.01); *A61B 6/585* (2013.01); *G06T 2210/41* (2013.01)

(56) References Cited

U.S. PATENT DOCUMENTS

| | | |
|---|---|---|
| 2010/0303200 A1 | 12/2010 | Kimchy et al. |
| 2011/0142316 A1 | 6/2011 | Wang et al. |
| 2014/0270440 A1 | 9/2014 | Inglese et al. |

OTHER PUBLICATIONS

Lifshitz, R., Kimchy, Y., Gelbard, N., Leibushor, A., Golan, O., Elgali, A., Hassoon, S., Kaplan, M., Smirnov, M., Shpigelman, B., Bar-Ilan, O., Rubin, D., Ovadia, A., "An X-Ray Based Capsule for Colorectal Cancer Screening, incorporating Single Photon Counting Technology", SPIE Physics of Medical Imaging, 2017.

Hsieh, J., "Computed Tomography", SPIE Press, (2003).

Padole, A., "CT Radiation Dose and Iterative Reconstruction Techniques", American Journal of Roentgenology, 204, pp. 384-392, (2015).

Rigaud, G., Nguyen, M.K., Louis, A.K., "Modeling and simulation results on a new Compton scattering tomography modality", Simulation Modelling Practice and Theory, 33, pp. 28-44, (2013).

Knoll, G. F., "Radiation detection and measurement", John Wiley & Sons, (2000).

Hubbell, H., Seltzer, S., M., "X-Ray Mass Attenuation Coefficients", NIST, https://www.nist.gov/pml/x-ray-mass-attenuation-coefficients, (1996).

Lifshitz, R., Nawi-Srur, S., Katz, B., Milman, L., Gubich, D., Lewkowicz, S., Kimchy, Y., "Phantom system for intraluminal x-ray imaging of the human colon", SPIE Physics of Medical Imaging, 2017.

Lagarias, J.C., J. A. Reeds, M. H. Wright, and P. E. Wright, "Convergence Properties of the Nelder-Mead Simplex Method in Low Dimensions", SIAM Journal of Optimization, 9(1), pp. 112-117, pp. 146-147, (1998).

Rubin D., Lifshitz, R., Bar-Ilan O., Weiss N., Shapiro Y., Kimchy Y., "Reconstruction method for x-ray imaging capsule", Proc. SPIE 10132, Medical Imaging 2017: Physics of Medical Imaging, 101324S (Mar. 9, 2017); doi:10.1117/12.2255051.

IMAGE RECONSTRUCTION WITH RADIOACTIVE IMAGING CAPSULE

RELATED APPLICATIONS

The present application claims priority from U.S. Provisional application No. 62/369,217 filed on Aug. 1, 2016, the disclosure of which is incorporated herein by reference.

TECHNICAL FIELD

The present disclosure relates generally to reconstructing an internal image of a patient's colon using an intra-lumen radioactive imaging capsule.

BACKGROUND

One method of examining the gastrointestinal tract for the existence of polyps and other clinically relevant features that may provide an indication regarding the potential of cancer is performed by ingesting an imaging capsule that will travel through the entire gastrointestinal (GI) tract and view the patient's situation from inside. In a typical case the trip can take between 24-72 hours, after which the imaging capsule exits in the patient's feces. When using visible light images may be transmitted directly to an external receiver and combined to form a reconstructed image of the patient's colon. However visible light requires the patient to perform extensive preparations of cleaning out the colon to prevent content from obstructing the imaging process.

Alternatively, an imaging capsule that uses radiation can be used to examine the colon without first cleansing it. Typically the patient ingests a contrast agent to enhance the imaging ability of the imaging capsule. Then the patient ingests the imaging capsule to examine the gastrointestinal tract while flowing through the contrast agent. The imaging capsule typically includes a radiation source, for example including a radioisotope that emits X-rays and/or Gamma rays. The radiation is typically collimated to allow it to be controllably directed in a specific direction during the imaging process. The imaging capsule is designed to measure Compton back-scattering and/or X-ray fluorescence and transmits the measurements (e.g. a count rate of photons having specific energies) to an external analysis device, for example a computer or other dedicated instruments.

In a typical implementation a radio-opaque contrast agent is used so that a position with a polyp will have less contrast agent and will measure a larger Compton back-scattering count and reduced X-ray fluorescence count to enhance accuracy of the measurements.

U.S. Pat. No. 9,037,219 to Baum et al. the disclosure of which is incorporated herein by reference, describes a system and method of estimating distances in the colon with an imaging capsule. The resolution of the reconstructed image is dependent on the accuracy of the estimated distances therefore there is a need for alternative and/or improved methods of measuring distances within the colon to enhance the accuracy of the images.

SUMMARY

An aspect of an embodiment of the disclosure relates to a system and method for reconstructing an image of a colon. Reconstruction is performed by a computer program executed on a computer or other dedicated computing hardware (for example ASIC or circuit with a processor and memory). The program receives scan data of a colon taken by an imaging capsule that is ingested by a person and travels along the gastrointestinal tract of the person. Optionally, when the capsule reaches specific locations such as the colon it is activated to scan the inner walls of the colon and transmit the scan data directly or indirectly to a computer for storing and analyzing the data. As the imaging capsule advances at each position the imaging capsule scans a slice of the colon, so that the computer can then reconstruct each slice and combine the slices to form a complete image of the colon.

In an exemplary embodiment of the disclosure, the imaging capsule emits X-ray radiation to scan inside the colon. The imaging capsule includes detectors that count photons returned toward the imaging capsule in response to the emitted radiation. The returned photons are produced by Compton backscattering and X-ray fluorescence or possibly a different scattering process. Optionally, the radiation source of the imaging capsule rotates while scanning to scan the entire circumference of an inner wall of the colon. The scanning data may include counts from each detector for a specific position in the colon or may include counts and angles, for example representing counts from scanning a portion of the inner wall at a specific position (e.g. a quarter, a third, a half).

The program receives the scan data and attempts to determine what geometric shape of inner wall of the colon would provide the given count values (for example for each slice of the colon). The program is designed to use a forward model based algorithm, where the forward model is a set of mathematical rules/formulas describing to some approximation the physical properties of the radiation path produced by the capsule, including interactions with the surrounding human physiology. The forward model is designed to convert the given geometrical description into expected count-rate readings at the capsule radiation detectors. The proposed reconstruction program starts with an initial guess of the colon geometry and applies the forward model to calculate from the geometry what counts would be expected from the detectors. The program then compares the calculated values with the measured data and checks to see how close they are. If they are close enough then the geometry is assumed to be correct. Otherwise the geometry is updated and the process is repeated iteratively until an optimal match is achieved.

One possible forward model is called a piecewise forward model that estimates the count of each detector based on examining the emitted radiation and the effect it has on each voxel of the space surrounding the imaging capsule. Another possible forward model is called a Gaussian forward model that estimates the count of each detector based on the location of the detector (e.g. the relative angular distance between each emitting beam and each detector), and the distance of the capsule center from the inner walls of the contour of the colon.

There is thus provided according to an exemplary embodiment of the disclosure, a method of reconstructing an image of a colon, comprising:

Receiving scan data of a colon taken by an imaging capsule that traverses the colon from the inside; wherein said imaging capsule emits X-ray radiation inside the colon and includes detectors that detect photons that are returned toward the imaging capsule from X-ray fluorescence interactions and Compton back scattering interactions responsive to the X-ray radiation; and wherein the scan data includes counts of photons detected by each detector from X-ray fluorescence interactions and Compton back scattering interactions;

Defining an initial guess of a geometry of a contour of a slice of the colon;

Calculating count values for each detector responsive to the defined geometry using a forward model;

Comparing the calculated count values of each detector with the values from the scan data;

If the results of the comparison do not indicate reaching an optimal match then adjust the defined geometry and repeat the calculating and comparing;

Otherwise if an optimal match is achieved store the geometry to represent the slice.

In an exemplary embodiment of the disclosure, the imaging capsule is first tested to determine calibration values required for performing said calculating. Optionally, the initial guess of the geometry of a slice of the colon is a specific shape. In an exemplary embodiment of the disclosure, the initial guess of the geometry of a slice of the colon is determined from a previously determined geometry of an adjacent slice of the colon. Optionally, the forward model encapsulates all physics processes necessary to estimate the count of each detector. In an exemplary embodiment of the disclosure, the forward model is a piecewise forward model that estimates the count of each detector based on the emitted radiation and an estimated response by each voxel of a space surrounding the imaging capsule. Alternatively, the forward model is a Gaussian forward model that estimates the count of each detector based on the relative angular distance between each emitting beam and each detector, and the distance of the capsule center from the contour of the colon. In an exemplary embodiment of the disclosure, the optimal match is determined by using least means square or maximum likelihood to determine whether the results of the comparing have a difference less than a preselected threshold value. Optionally, the scan data includes position information of the imaging capsule in the colon with the detector counts, wherein the position information is determined independently of the detector counts. In an exemplary embodiment of the disclosure, the scan data includes a plurality of measurements comprising sets of detector counts and rotation angles of a radiation source for each position in the colon. Optionally, the scan data includes detector counts of a scan of an entire circumference of each position in the colon. In an exemplary embodiment of the disclosure, adjusting the defined geometry includes increasing a distance from the imaging capsule to the colon contour for specific rotation angles of a radiation source and decreasing the distance from the imaging capsule to the colon contour for other rotation angles.

There is further provided according to an exemplary embodiment of the disclosure, a system for reconstructing an image of a colon, comprising:

A computer or dedicated programmable computing hardware, configured to receive scan data of a colon taken by an imaging capsule that traverses the colon from the inside; wherein said imaging capsule emits X-ray radiation inside the colon and includes detectors that detect photons that are returned toward the imaging capsule from X-ray fluorescence interactions and Compton back scattering interactions responsive to the X-ray radiation; and wherein the scan data includes counts of photons detected by each detector from X-ray fluorescence interactions and Compton back scattering interactions;

A computer program configured to be executed on the computer or dedicated programmable computing hardware and perform the following:

Defining an initial guess of a geometry of a contour of a slice of the colon;

Calculating count values for each detector responsive to the defined geometry using a forward model;

Comparing the calculated count values of each detector with the values from the scan data;

If the results of the comparison do not indicate reaching an optimal match then adjust the defined geometry and repeat the calculating and comparing;

Otherwise if an optimal match is achieved store the geometry to represent the slice of the colon.

In an exemplary embodiment of the disclosure, the imaging capsule is first tested to determine calibration values required for performing said calculating. Optionally, the initial guess of the geometry of a slice of the colon is a specific shape. In an exemplary embodiment of the disclosure, the initial guess of the geometry of a slice of the colon is determined from a previously determined geometry of an adjacent slice of the colon. Optionally, the forward model encapsulates all physics processes necessary to estimate the count of each detector. In an exemplary embodiment of the disclosure, the forward model is a piecewise forward model that estimates the count of each detector based on the emitted radiation and an estimated response by each voxel of a space surrounding the imaging capsule. Alternatively, the forward model is a Gaussian forward model that estimates the count of each detector based on the relative angular distance between each emitting beam and each detector, and the distance of the capsule center from the contour of the colon. In an exemplary embodiment of the disclosure, the optimal match is determined by using least means square or maximum likelihood to determine whether the results of the comparing have a difference less than a preselected threshold value. Optionally, the scan data includes position information of the imaging capsule in the colon with the detector counts, wherein the position information is determined independently of the detector counts. In an exemplary embodiment of the disclosure, the scan data includes a plurality of measurements comprising sets of detector counts and rotation angles of a radiation source for each position in the colon. Optionally, the scan data includes detector counts of a scan of an entire circumference of each position in the colon. In an exemplary embodiment of the disclosure, adjusting the defined geometry includes increasing a distance from the imaging capsule to the colon contour for specific rotation angles of a radiation source and decreasing the distance from the imaging capsule to the colon contour for other rotation angles.

There is further provided according to an exemplary embodiment of the disclosure, a non-volatile computer storage medium for storing a program to execute the method described above.

BRIEF DESCRIPTION OF THE DRAWINGS

The present disclosure will be understood and better appreciated from the following detailed description taken in conjunction with the drawings. Identical structures, elements or parts, which appear in more than one figure, are generally labeled with the same or similar number in all the figures in which they appear, wherein.

DETAILED DESCRIPTION

Figure 1:
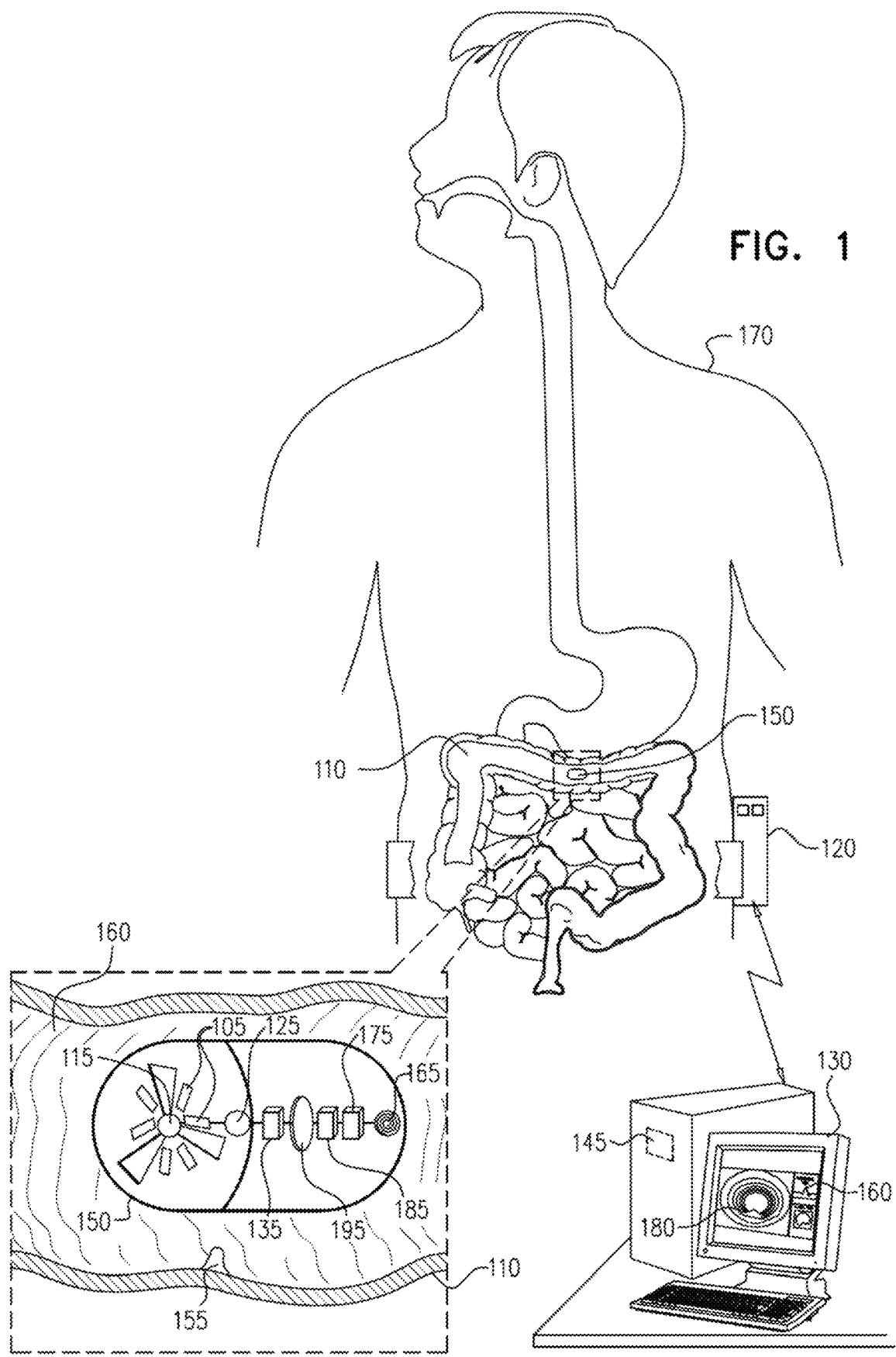
FIG. 1 is a schematic illustration of a system for reconstructing an image of a colon, according to an exemplary embodiment of the disclosure.

FIG. 1 is a schematic illustration of a system 100 for imaging a colon 110, according to an exemplary embodiment of the disclosure. System 100 includes an imaging capsule 150 that is ingested by a patient 170 to examine the patient's gastrointestinal tract (for example the colon 110) from the inside. In an exemplary embodiment of the disclosure, imaging capsule 150 includes a radiation source 115, for example Os 191 or W 181 emitting Xray and/or Gamma rays with sufficient energy to examine the internal structure of the colon 110. Optionally, the radiation is collimated with one or more collimators 125 to direct the radiation in desired directions, for example by rotating the collimator with a motor 135. Likewise imaging capsule 150 may include a power source 195 such as a battery to power the motor 135 and other elements that need electrical power. In an exemplary embodiment of the disclosure, imaging capsule 150 includes detectors 105 to sense photons returned approximately toward imaging capsule 150 in response to the radiation emitted by the radiation source 115. Optionally, the detectors 105 may be designed to count X-ray/Gamma photons of specific energies.

In an exemplary embodiment of the disclosure, the information recorded by the detectors 105 is transmitted by a transceiver 185 from the imaging capsule to an external recorder 120 that records the information. Optionally, the information includes: a count, energy level, rotation angle of the collimator, and/or the identity of the detector providing the information. External recorder 120 records the information for analysis by a general purpose computer 130 after the imaging capsule 150 exits from within the patient 170. Alternatively, the information may be processed in real time to enable a live display of the gastrointestinal tract/colon 110 while the capsule is advancing therein.

In an exemplary embodiment of the disclosure, computer 130 uses a program 145 for reconstructing an image of the colon 110 based on the recorded information from the detectors 105. Optionally, program 145 assumes an initial geometry for each slice of the colon 110 (e.g. based on a previous adjacent slice). In an exemplary embodiment of the disclosure, program 145 uses a forward calculation to determine what the expected values recorded from the detectors should be based on the given geometry. Program 145 then compares the calculated values with the recorded values and iteratively updates the geometry and repeats the calculations until reaching a good agreement between the calculated values and the recorded values.

In an exemplary embodiment of the disclosure, imaging capsule 150 further includes transmission coils 165 and/or an accelerometer 175 to track motion of the imaging capsule 150, for example to scan a slice of the internal structure of the colon 110 every time the capsule advances through the colon 110 or changes its direction. Optionally, the transmission coils 165 enable tracking the position of the imaging capsule 150 relative to the external recorder 120 and the accelerometer 175 enables tracking angular rotation of the imaging capsule 150. Alternatively, the imaging capsule 150 may scan continuously, periodically or based on a different controlled or independent temporal plan throughout the colon 110. In some embodiments of the disclosure, the position information helps to reconstruct an image of the colon 110 by following the position of each reconstructed slice.

In an exemplary embodiment of the disclosure, the patient 170 additionally ingests a contrast agent 160, for example water mixed with iodine. The contrast agent fills the colon 110 so that the imaging capsule 150 essentially advances through the colon 110 while surrounded by contrast agent 160. Optionally, the detectors 105 of the imaging capsule 150 separately count photons that originate from Compton Backscatter (CMT) and photons from X-ray fluorescence (XRF) (e.g. the detectors 105 having energy windows and separately counting photons of a specific energy range). Optionally, after a specific time duration (e.g. every millisecond or every second) the count from each detector 105 is transmitted to external recorder 120 for analysis.

Figure 2B:
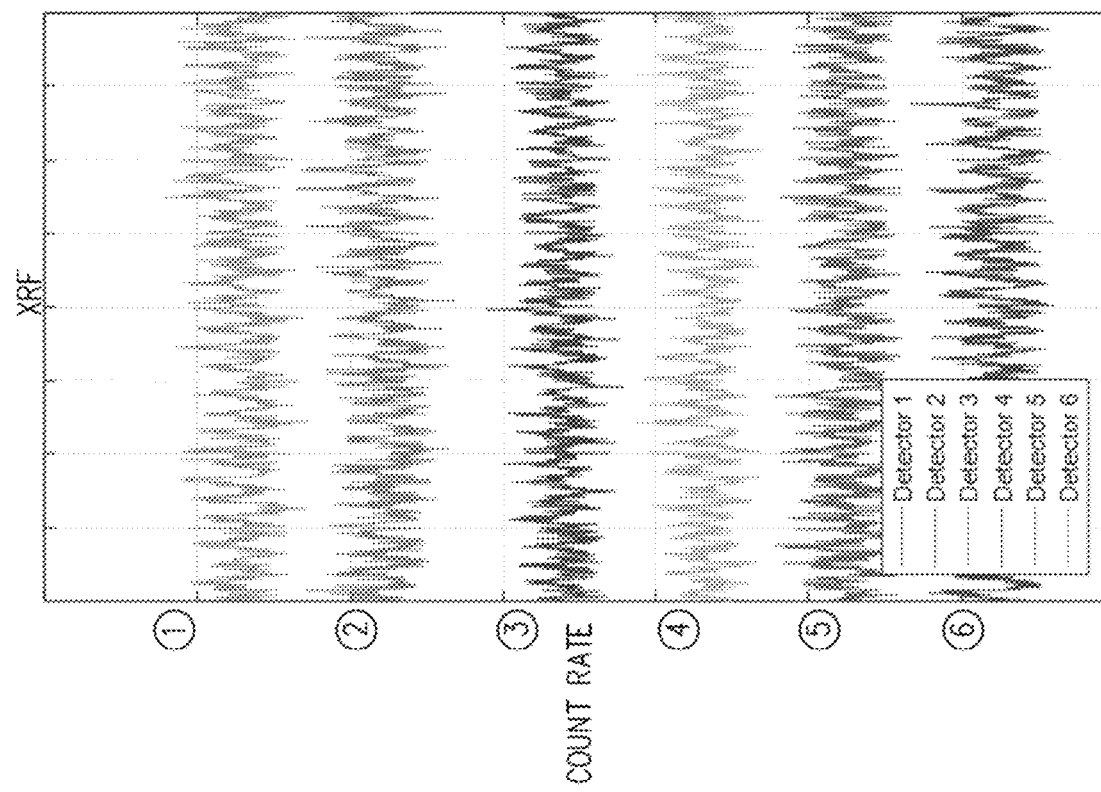
FIG. 2A-B are schematic illustrations of graphs of photon counts of (A) Compton Backscatter (CMT) and (B) X-ray fluorescence (XRF) detected by multiple detectors surrounding in a capsule, according to an exemplary embodiment of the disclosure.
Figure 2A:
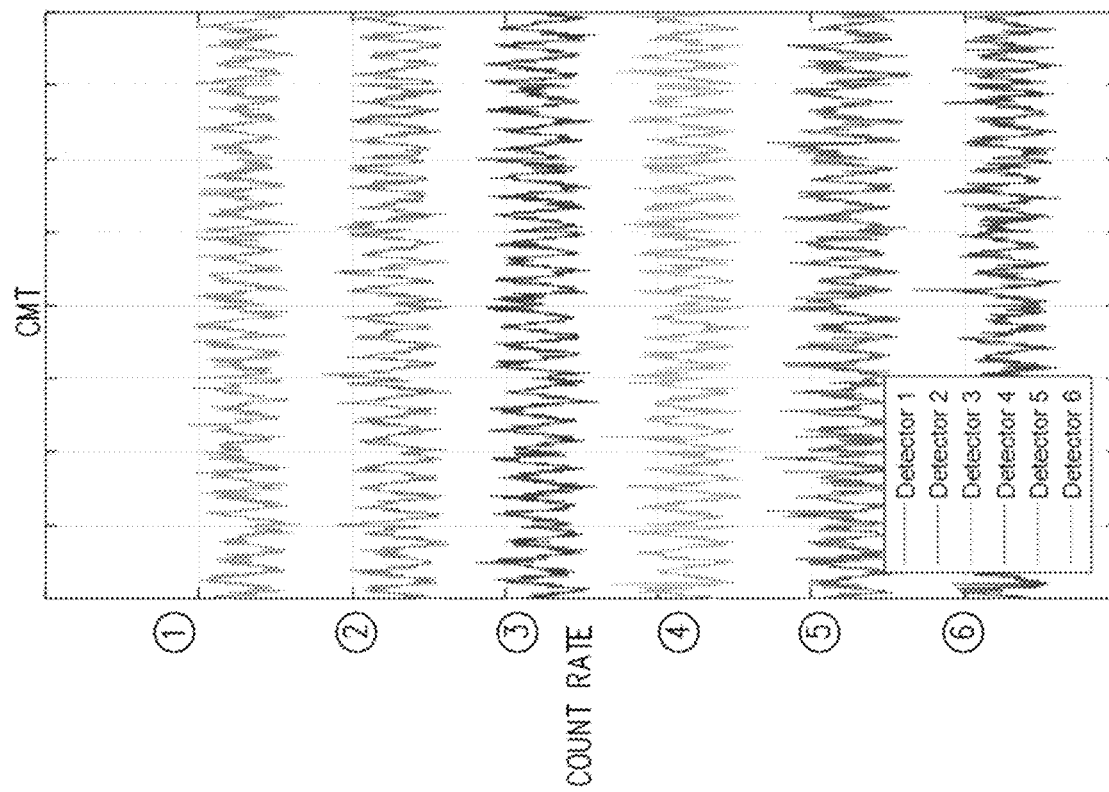
Figures 3A, 3B, 3C:
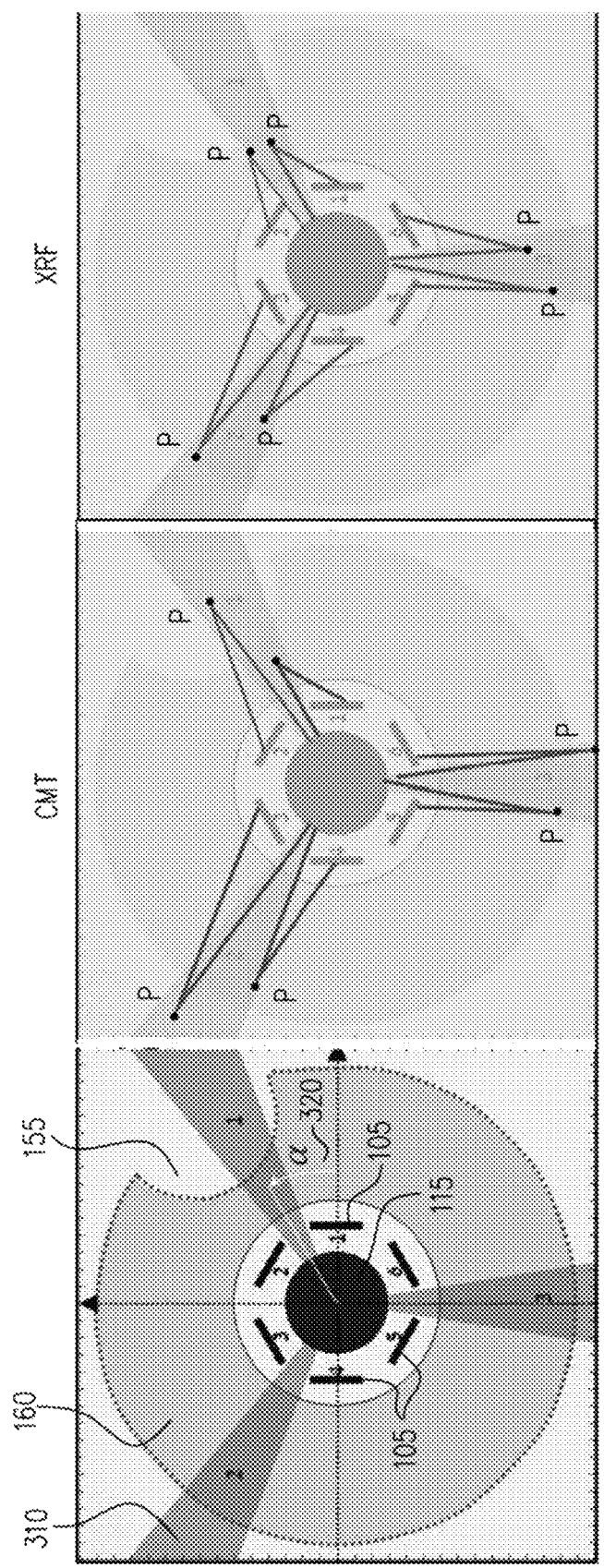
FIG. 3A-C are schematic illustrations of a cross sectional view of the imaging capsule exemplifying forming a count, according to an exemplary embodiment of the disclosure.

FIG. 2 is a schematic illustration of a graph of transmitted photon counts of (A) Compton Backscatter (CMT) and (B) X-ray fluorescence (XRF) from multiple detectors 105 surrounding the radiation source 115 of an imaging capsule 150, according to an exemplary embodiment of the disclosure. FIG. 3 is a schematic illustration of a cross sectional view of imaging capsule 150 exemplifying forming a count, according to an exemplary embodiment of the disclosure.

In an exemplary embodiment of the disclosure, the collimators emit radiation in multiple beams 310 (e.g. 3 collimated beams). Multiple detectors 105 (e.g. 6 detectors) are positioned around the collimated beams 310 to detect particles that return approximately back toward the radiation source due to Compton Backscattering and/or X-ray fluorescence. The collimated beams 310 may be rotated around an axis extending perpendicular to the page to scan the entire inner circumference of the colon. For example in FIG. 3 by rotating angle 320 by 120° the beams 310 scan the entire circumference once. By rotating angle 320 by 360° the circumference is scanned three times. Optionally, for each position in the colon the imaging capsule 150 performs multiple scans to enhance resolution and accuracy of the measured results.

In an exemplary embodiment of the disclosure, the imaging capsule 150 advances from one position to another and provides scan data of the colon slice by slice. The scan data transmitted to external receiver 120 may include the detector values for each position or the scan data may be of a higher resolution, for example including detector values for every preselected angle, for example for every 30°, 60° or 90° or rotation in a specific position. Optionally, the scan data may then include the detector counts and the angle at which they were sampled, for example sampling four times in a rotation at 90°, 180°, 270° and 360°.

In an exemplary embodiment of the disclosure, the source of X-ray radiation is a radioisotope (Os 191 or W 181), whose radiation in the relevant energy band is quasi-monoenergetic producing X-ray photons at a given energy $E_0$ (65 and 57 keV respectively). The radiation path underlying the physical model of the capsule can be abstracted as follows: a ray of photons of energy $E_0$ and intensity $I_0$ is emitted by the radiation source at the direction $\theta_F$ (where F stands for Forward) towards a point p in space. Some of the photons are absorbed or scattered on the path to p, while $I_F$ photons reach it. In the vicinity of point p, $\mu_{Photo}$ is the fraction of photons absorbed through the photoelectric effect, and $\mu_{CMT}$ is the corresponding fraction for Compton scattering. The rest go further in direction $\theta_F$. In the exemplary embodiment of the invention, two types of radiation paths are considered the main role-players for the imaging principle: the Compton (CMT) radiation path and X-ray fluorescence (XRF) radiation path. Other radiation paths, e.g. coherent scattering and secondary interactions are less significant, thus can be neglected.

FIG. 3 (B) shows a CMT radiation path—a ray of photons that are scattered backwards in direction $\theta_B$ and intersects one of the capsule detectors 105. Given $\theta_B$ one can use the Klein-Nishina formula, to calculate the number of photons scattered in that direction $I_B^{CMT}$ their energy $E_B^{CMT}$. For instance, the beam of photons with original $E_0$=60 keV backscattered at 180° would possess ~48.5 keV energy, and for a solid angle of 1° would represent ~0.3% of the total number of scattered photons. This ray of photons undergoes absorption and scattering until it reaches detector d bearing intensity $I_{Bdet}^{CMT}$. FIG. 3 (B) depicts several CMT ray traces, where the sharp turns (edges) correspond to the point of interaction p. One can see that CMT events occur both inside and outside the colon wall.

FIG. 3 (C) shows an XRF radiation path—In case point p is inside the colon filled with the iodinated contrast agent 160, part of the photoelectric absorption occurs in atoms of iodine. These atoms then emit characteristic X-ray photons with energy $E_B^{XRF}$ which, for Iodine, is known to be concentrated around 28.6 keV ($K_\alpha$ line). Thus, we can consider a ray of XRF photons emitted in direction $\theta_B$ intersecting one of capsule detectors. X-ray fluorescence is known to be distributed equally in all directions, so the intensity of the photon ray $I_B^{XRF}$ is solely determined by the fraction of its solid angle. FIG. 3 (C) depicts several arbitrary XRF ray traces. One can see that XRF events occur only inside the colon.

In an exemplary embodiment of the disclosure, the X-ray detectors 105 employed in the capsule are parts of photon counting channels capable of separating between two (or more) energy ranges. Using an energy calibration procedure, the channels are set up so that the low energy bin counts photons originating from Iodine XRF, and the high-energy bin counts photons originating from CMT. Optionally, the greater the distance from the radiation source 115 to the inner walls of the colon 110 the greater the count of XRF, whereas the CMT count is the opposite.

In an exemplary embodiment of the disclosure, the base reconstruction problem can be defined as follows: Consider detectors d=1 . . . dmax, energy bins e={CMT,XRF}, and capsule angular positions $\alpha$=1 . . . n, and denote the corresponding detector readings $R_{de\alpha}$, it is required to provide the description of the colon wall in terms of distances from capsule center $r(\theta)$ for $0 \leq \theta < 360°$. In an exemplary embodiment of the disclosure, any deviation from a perfect circle will result in a difference between the counts of each detector d, especially polyps or other clinical abnormalities will affect the counts of some of the detectors.

In an exemplary embodiment of the disclosure, for each slice of the colon 110 an initial geometric shape is assumed (represented by $r(\theta)$), for example a circle or ellipse or the same shape as a previous slice of the colon 110. Optionally, a forward model is used to calculate the expected values of the detectors 105 based on the geometric shape. If the calculated values are the same as the measured values then it is assumed that we have discovered the correct geometry of the colon. Otherwise the geometric shape is corrected and the expected values are recalculated. This process is repeated until the expected counts match the measured counts.

Following is a first method of implementing a forward model to calculate detector count values:

Piecewise Forward Model:

In an exemplary embodiment of the disclosure, to develop a forward model that allows transforming a geometry into an expected detector readout, we divide the volume surrounding the radiation source 115 into small voxels. Optionally, Beer-Lambert and Klein-Nishina formulas and attenuation coefficients tables can be applied for modeling propagation, scattering, and XRF generation. In an exemplary embodiment of the disclosure, for the forward model to function as an optimal engine of an iterative reconstruction algorithm, certain assumptions are made to simplify the calculation process. The assumptions may include that the propagation medium is assumed to be a compound of only two materials—soft tissue and Iodine, where absorption and scattering properties are scaled using variable density factors. Only primary scatter and XRF products reaching capsule detectors are of interest in the model, all other processes that do not influence, or negligibly influence the detectors, are disregarded. The sequence of calculations performed is such that the environment-independent parts that depend only on capsule configuration are executed first, so that the iterative algorithm can compute them once, and then apply only the remaining variable part for the converging description of the environment.

Figure 4:
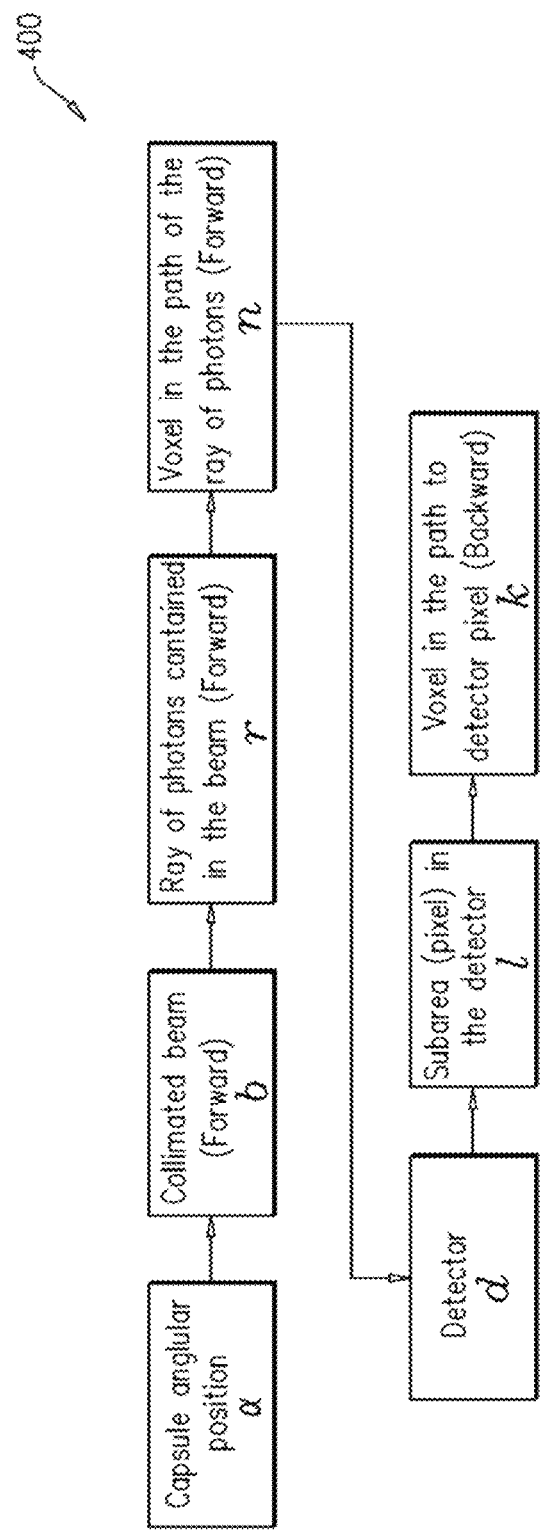
FIG. 4 is a schematic illustration of a hierarchy of sub-elements taking part in an imaging capsule radiation path, according to an exemplary embodiment of the disclosure.
Figure 5:
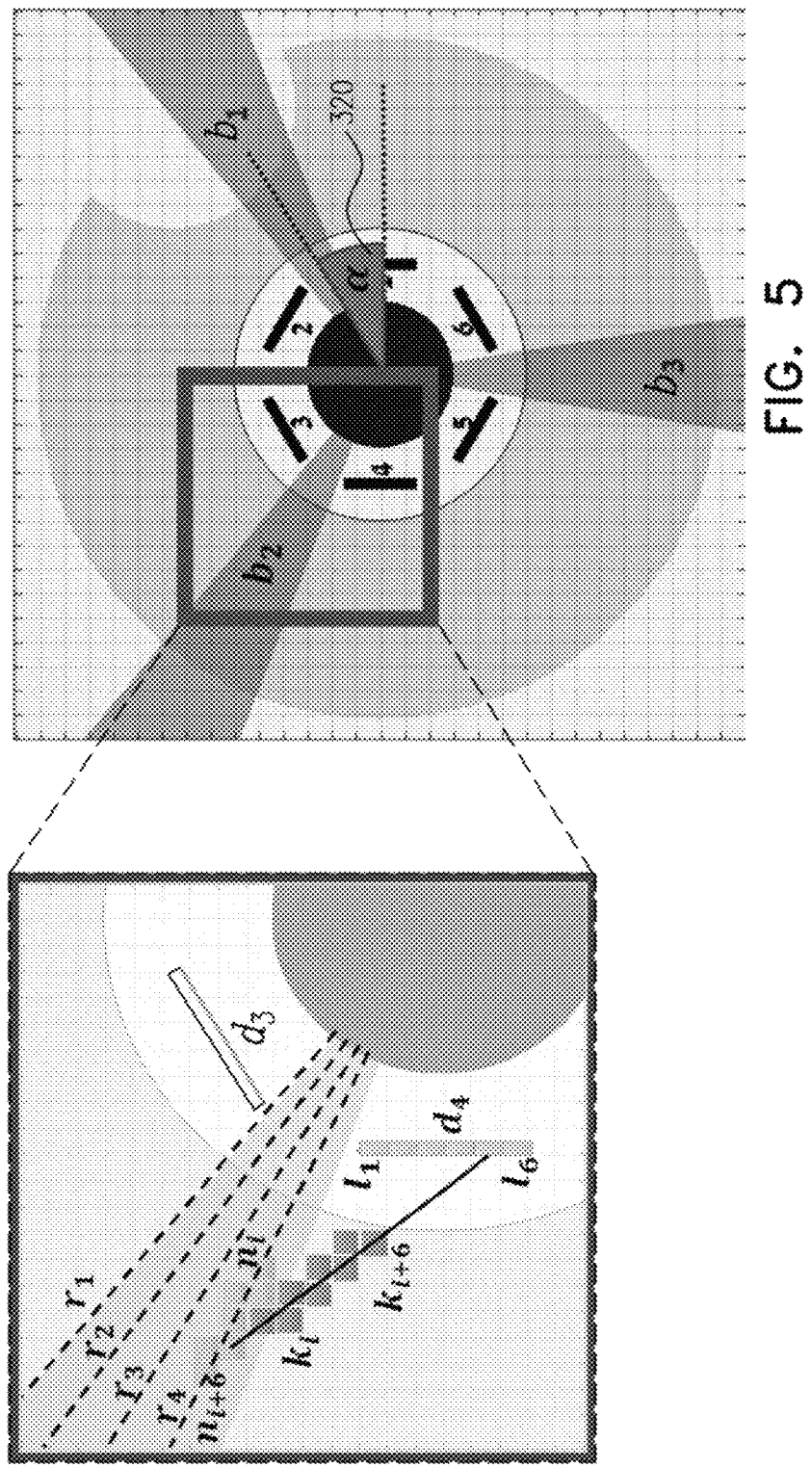
FIG. 5 is a schematic illustration of implementation of the piecewise forward model in a diagram of an imaging capsule, according to an exemplary embodiment of the disclosure.

Derivation of the Calculations Involved in the Piecewise Forward Model:

In the proposed piecewise forward model, the radiation path is assumed as described above. The mathematical equations governing the behavior of the participating elements are discussed below. The conceptual interrelation between the elements being processed is depicted in FIG. 4, which is implemented as a hierarchy 400 of indices. For instance, for each ray of photons—r, there exists a collection of voxels n=1 . . . $n_{max}$, where each voxel may be the origin of a CMT or XRF ray of photons towards any of the detectors d=1 . . . $d_{max}$, etc. This idea is also illustrated in FIG. 5 as an implementation 500 of rays propagating forward and producing photons that travel backward toward the detector.

The description of the environment surrounding the capsule can be defined as a distribution of the densities of two basic materials: iodine and soft tissue, while in the current context soft tissue can be considered equivalent to water with a higher density. As the space is divided into voxels, this distribution is denoted as $\rho_p^M$ where p is the unique spatial index of the voxel and M represents the basic material M={1,2}≡{Soft tissue, Iodine}.

We also define $\mu^{MA}$ as an attenuation coefficient of material M, with respect to the attenuation process A={1,2}≡{Compton, Photoelectric} at the nominal energy of capsule's radioisotope. $\mu^M = \mu^{M1} + \mu^{M2}$ is the total attenuation coefficient at the nominal energy of material M.

The number of photons absorbed in voxel n in the path of ray r of beam b, by the absorption mechanism A is obtained using equation (1):

$$I_{brnA}^B = \left(\Lambda_{brn}^F \cdot \sum_{M=1,2} \mu^{MA} \cdot \rho_{P_{brn}}^M\right) \cdot I_{br}^F \cdot \exp\left(-\sum_{m=1}^{n-1}\left(\Lambda_{brm}^F \cdot \left(\sum_{M=1,2} \mu^M \cdot \rho_{P_{brm}}^M\right)\right)\right) \quad (1)$$

Where three matrices containing the mathematical description of the capsule geometry are employed:

$$I_{br}^F, P_{brn}^F, \Lambda_{brn}^F.$$

IWherein I represents ray intensity, P—is a mapping matrix associating voxels traversed by a ray with voxel's spatial index and Λ represents path lengths of the rays within voxels. Superscript F stands for "Forward", indicating that the entities are of the primary photon rays that originate in the radiation source 115. The output intensity matrix is assigned a superscript B (Backward), as the number of photons that are reduced from the primary ray in specific voxel is indicative of the number of secondary photons generated by the voxel either by CMT or XRF, among them those that are directed to the capsule detectors.

The predicted count rate to be measured by capsule detectors is given in equation (2), which models the propagation of the rays towards capsules detectors, from the intensities that were calculated in equation (1).

$$I_{dba} = \sum_{l,r,n} I_{brnAdl}^B \cdot \exp\left(-\sum_{M=1,2} \mu_{brnAdl}^M \cdot \left(\sum_k \Lambda_{brndlk}^B \cdot \rho_{P_{brndlk}}^M\right)\right) \quad (2)$$

Where the ray intensity matrix $I_{brnAdl}^B$ is the derivative of the number of photons absorbed in a voxel, representing the portion emitted towards the detector pixel. This matrix is calculated by considering detectors solid angle and scattering cross-section derived by means of the Klein-Nishina formula applied to the rays scattering angle.

The rays travelling in the backward direction possess photon energy that is reduced in comparison to the energy $E_0$ of the radioisotope, and is equal either to Iodine XRF energy or to the Compton scattered energy, dependent on the scatter angle and derived from the Klein-Nishina formula. Photon energies affect the attenuation coefficients, as reflected in calculation of the attenuation coefficient matrix $\mu_{brnAdl}^M$.

Implementation of the Piecewise Forward Model:

In order to take the full advantage of the mathematical model described in equations 1 and 2, the calculation should be implemented in such a way that the computations independent of $\rho_p^M$, namely building the matrices $I_{br}^F$, $P_{brn}^F$, $\Lambda_{brn}^F$, $P_{brndlk}^B$, $\Lambda_{brndlk}^B$ and $\mu_{brnAdl}^M$ is performed first. The rest of the calculation, which consists of executing equations 1 and 2, may then be performed several times, each time being applied to a different description of the environment. This way, the main objective of developing the forward model this way is achieved, as the computation is divided so that the heavy part is performed once, while each separate iteration is significantly faster.

In an exemplary implementation, the procedure described here has been successfully implemented by means of MATLAB (© 1994-2015 The MathWorks, Inc.) and applied to several simulated scenarios, some of the results are shown below. In terms of computational performance, the time it takes to perform the initial heavy calculation is generally greater (e.g. about 75 times) the time required for each subsequent environment dependent iteration.

Figure 6A:
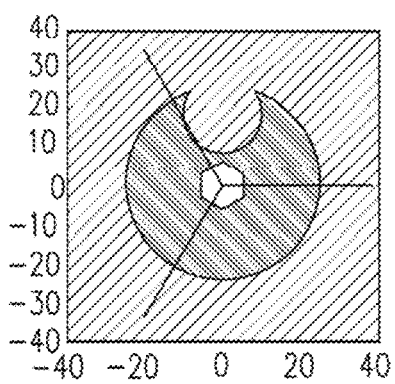
FIG. 6A-F are schematic illustrations exemplifying a piecewise forward model, wherein A shows a geometrical description of a simulated case, B and C show distribution of all XRF and CMT interactions in space surrounding the capsule, D and E show distribution of XRF and CMT interactions that influence the detectors, F and G show the detector readings for all samples along ⅓ of a rotation for CMT and XRF and the dashed line marks the angular position used for depicting FIGS. B, C, D and E, according to an exemplary embodiment of the disclosure.
Figure 6B:
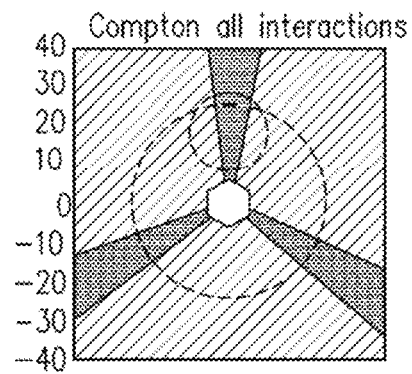
Figure 6C:
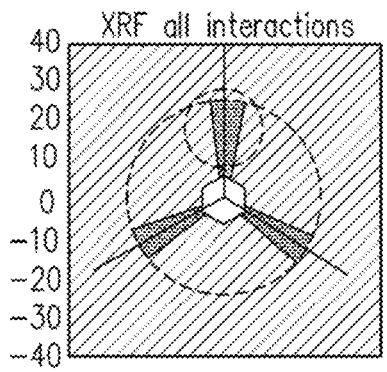
Figure 6D:
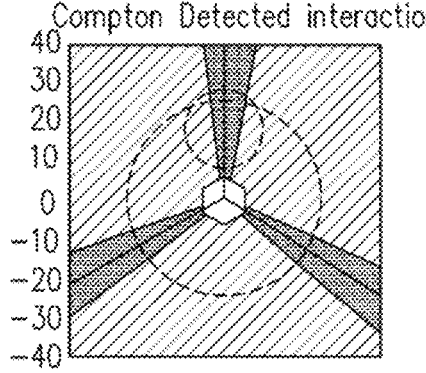
Figure 6E:
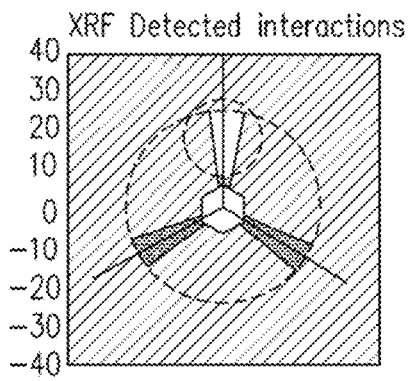
Figure 6F:
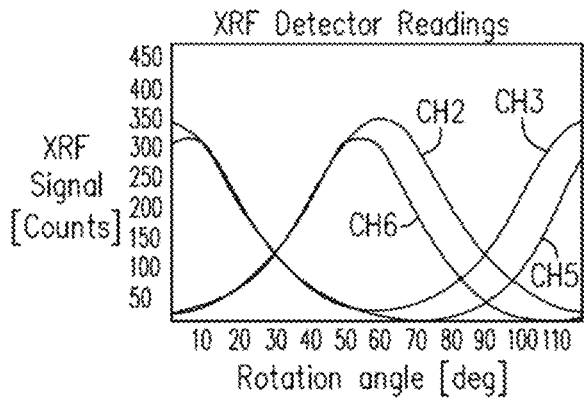
Figure 6G:
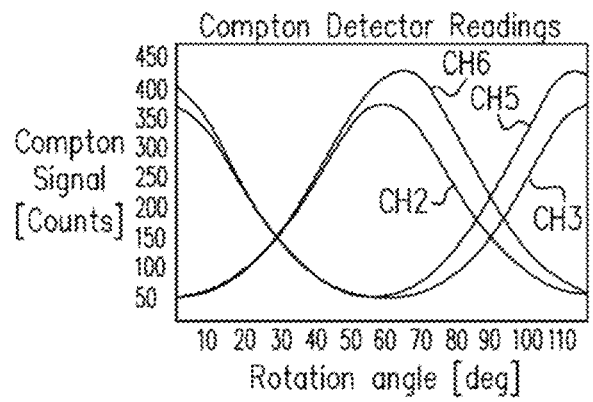
Figure 7A:
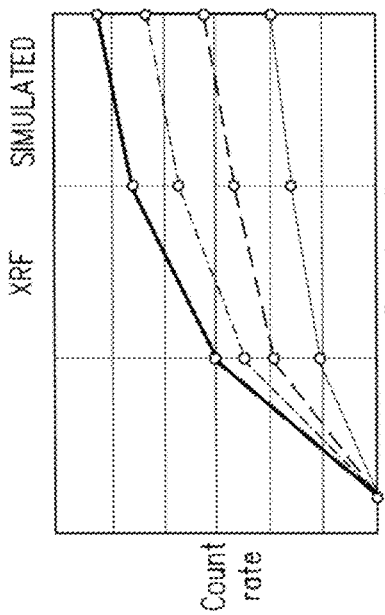
FIG. 7A-F are schematic illustration exemplifying simulation and measurements of barrel phantom scans, wherein A shows a schematic of the system, B and C show average detector readings for one detector for simulated CMT and XRF signals, D shows a schematic implementation of a phantom system, E and F show average detector readings for measured CMT and XRF signals, according to an exemplary embodiment of the disclosure.
Figure 7B:
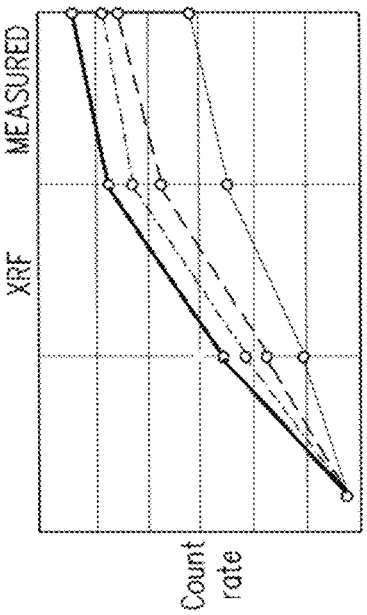
Figure 7C:
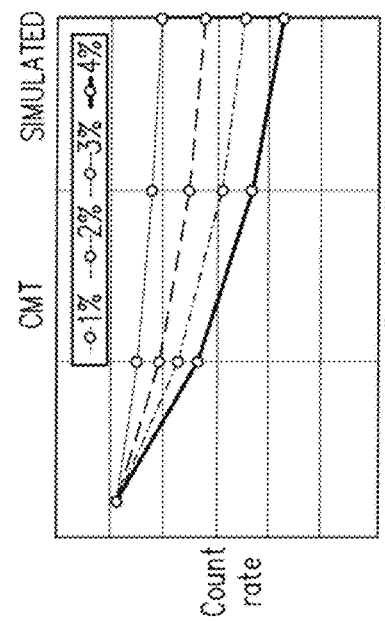
Figure 7D:
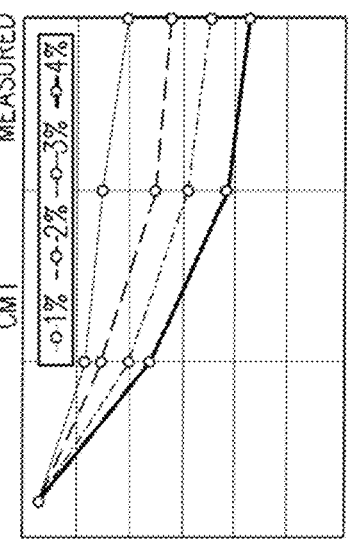
Figure 7E:
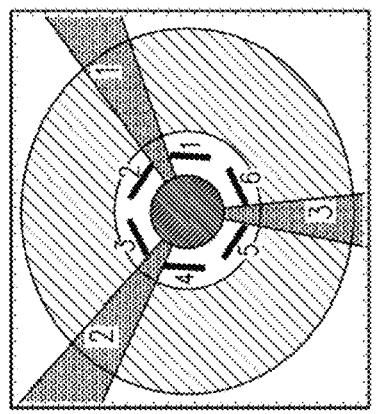
Figure 7F:
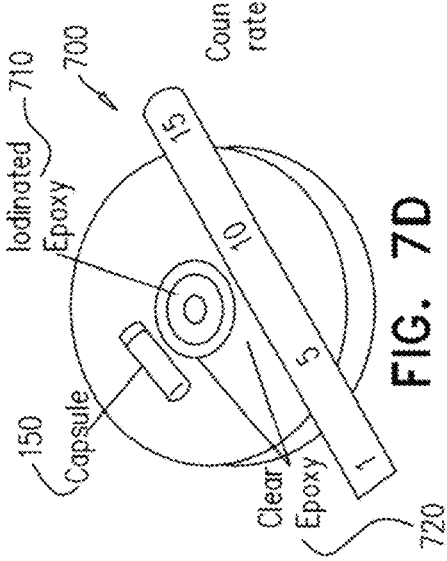

FIG. 6 shows the calculation results obtained for a synthetic case schematically shown in FIG. 6A (with a polyp 155 in the top area of a cross section of the colon 110). The capsule is symmetrically surrounded by a circular colon perimeter filled with uniformly Iodinated water-like medium (contrast agent 160). A circular polyp intrusion 155 is implemented on the top of the colon perimeter. In addition to applying equations 1 and 2 to obtain the simulated detector readings (FIGS. 6 F and G), in this case we also examine the intermediate products of the calculations to obtain the information on where the different interactions occur. This information is illustrated in FIG. 6 subfigures B, C, D and E by means of the depicted distribution maps generated for a single angular position of the capsule. FIG. 6-B and FIG. 6-C illustrate the output of equation 1 where each pixel in the map reflects the number of photons absorbed in the corresponding voxel due to Compton scattering and Photoelectric (X-ray fluorescence) absorption respectively. As expected, the photoelectric absorption is concentrated within the iodinated media, while the Compton scattering occurs both inside and outside the colon perimeter with a small emphasis at the location of boundary crossing. Similarly, FIG. 6-D and FIG. 6-E illustrate the output of equation 2, where each pixel in the map reflects the number of photons emitted from the corresponding voxel and eventually detected by one of the capsule detectors. One should note that, as indicated by the intensity bars on the right of the maps, intensities within secondary interaction maps detected by the capsule are significantly lower than those of the primary radiation.

In FIG. 6, one can see that the simulated polyp is most closely located to detector channels 2 and 3, although not facing neither of them directly. The angular beam position shown is when one of the beams is projecting towards the polyp, so we expect the readings of detectors 2 and 3 to reflect that. Indeed, one can see from FIG. 6-F that the Compton signal from these two detectors is higher than that of their symmetrical counterparts—channels 5 and 6. On the other hand, FIG. 6-G exhibits lower XRF signal for these detectors. These effects can be explained by observing the interaction distribution maps—the amount of XRF interactions is decreased as less iodinated contrast is interacting with the X-ray beam when exerted towards the polyp, while the backscattered CMT photons encounter less absorption when less iodine is present in their path. Obviously, the information contained in these elevated and reduced detector signals is to be converted into the description of the polyp by means of the reconstruction algorithm.

In an exemplary experiment to exhibit the validity of the piecewise model a series of simulations and actual measurements were performed using imaging capsule 150, on a set of so-called 'barrels'—circular epoxy phantoms 700 built of an internal part 710 that is uniformly mixed with iodine and external part 720 that is a clear epoxy. FIG. 7 A schematically shows the barrel measurement setting, and FIG. 7-D shows a photograph of an actual one. The series of measurements and simulations included various combinations of barrel radial sizes and the different concentrations of Iodine. For comparison, the resulting detector readings have been averaged over all scanned samples and plotted as function of iodinated-barrel radius—the effective distance to colon wall. FIGS. 7-B and C show these calculations for the simulated data, while FIGS. 7-E and F show the results for the measured data. The graphs corresponding to the simulated data and those corresponding to the measured data exhibit resemblance based on the monotonicity and the trends as function of barrel size and iodine density changes, convergence at high distances, and the detected counts order of magnitude.

Naturally, the measured and simulated values are not identical, as the exact physical properties of the specific capsule, such as its detector response, beam intensity and others were not included in the simulation. However by performing a proper calibration process these properties can be taken into account.

In some embodiments of the disclosure a simplified method can be used to serve as a forward model to calculate detector count values form a given geometry. This second model is referred to as a forward Gaussian Model (FGM), employing simpler mathematical equations developed as a simplification of the piecewise model.

Forward Gaussian Model (FGM):

In order to develop a simplified version of the forward model demonstrated in the previous section the following assumptions are made:

a. The signal measured by the detectors at each angular beam position depends only on the scanned region directly in front of the beam.

b. The detector readings are influenced by both the composition of the environment and on the relative angular distance between detectors and beams. Current assumption is that these two mechanisms of influence can be separated, so that the rate detected by detector d from beam b is equal to the product:

$$A_{dbe}(r(\theta_b)) \cdot G_{dbe}(\theta_b - \theta_d),$$

where $\theta_b$ and $\theta_d$ are the angles of the detector and the beams, $A_{dbe}$ is the function of the colon wall distance $r(\theta)$ and $G_{dbe}$ is a function of angular distance $\Delta\theta$. As in previous section, index e stands for the energy bin.

c. Overall detector reading is equal to the sum of the contributions from the different beams (b), thus it can be expressed as equation 3:

$$R_{de} = \sum_{b=1}^{3} A_{dbe}(r(\theta_b)) \cdot G_{dbe}(\theta_b - \theta_d) \quad (3)$$

Where $R_{de}$ stands for the reading of detector d at energy bin e.

Figure 8B:
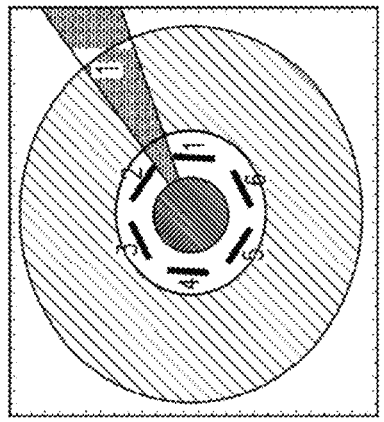
FIG. 8A-C are schematic illustrations exemplifying the effect of one or three beams on a detector, wherein A shows a schematic setup of a three beam system, B shows a schematic setup of a single beam system, C shows simulation results for a single beam and three beam system with barrels of different sizes, wherein the sizes are 0, 4, 9 and 14 mm between the detectors and the simulated colon wall, according to an exemplary embodiment of the disclosure.
Figure 8A:
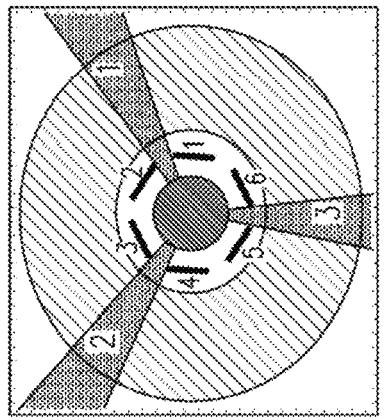
Figure 8C:
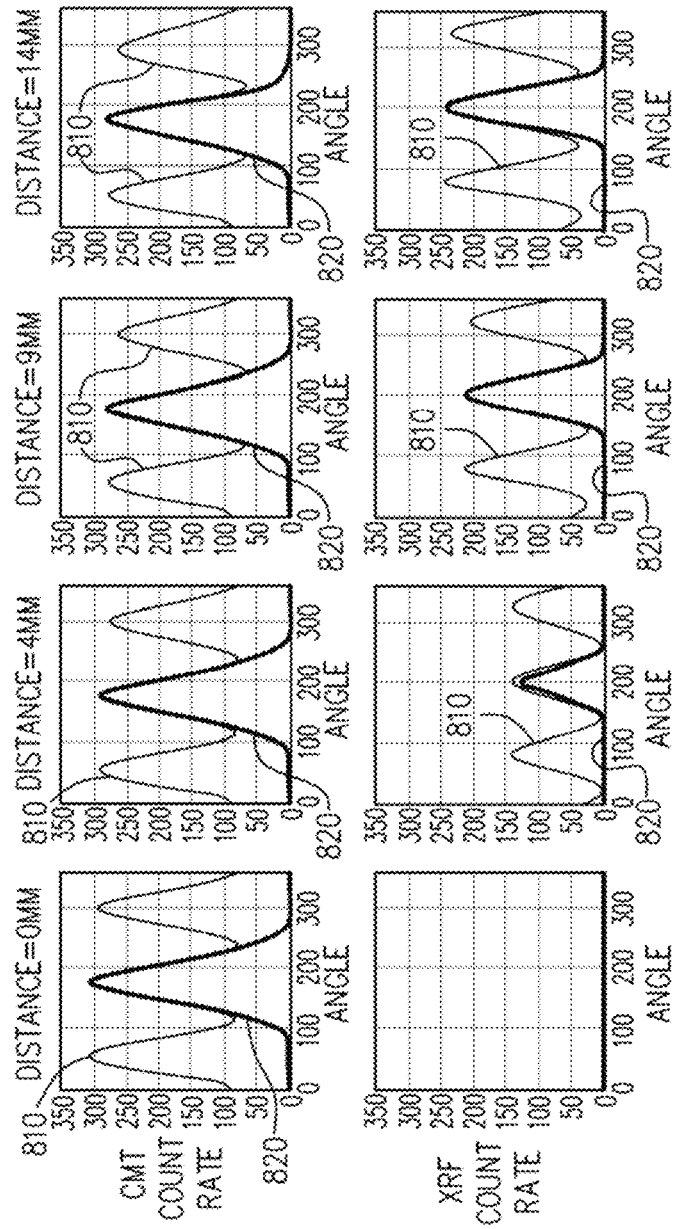

Devising the Angular Dependence Function:

To investigate the influence of the beam-to-detector angular distance, the piecewise forward model is used to simulate a scenario in which only one beam is emitting X-rays. This allows isolation of each beam influence on the detector. The results of this simulation in several barrel scenarios are shown in FIG. 8, also compared to the nominal three-beam case 810. The graphs in FIG. 8 C depict CMT and XRF signals measured by one of the detectors as a function of beam angular position. For the three-beam case 810 we observe modulation similar to the modulation already observed in FIG. 2 and FIG. 6. The single beam case 820 result, coincides with the central part of the three-beam case 810. This indicates that a beam that is in perfect alignment with a detector contributes most of the photons that are detected. Note also that the function reaches zero for approximately half a cycle, indicating that the beam does not affect the readings of the detector when the angular distance is significant, relative to 120o. The bell-like shape of this curve suggests approximating the angular dependence G G by a Gaussian function. Gaussian fit curves are already superimposed as 820 within FIG. 8 from which one can clearly see this is a good approximation. Therefore, we adopt the Gaussian function as the representative of the angular dependence G.

The Radial Dependence Function:

Looking at the simulation result for the different barrel sizes shown in FIG. 8, we observe the change of the amplitude of the approximating Gaussian functions it increases with barrel size for the XRF signal and decreases with the barrel size for the CMT signal. This amplitude change is consistent with assumption (b) made in the beginning of this section and the resulting equation (3). The amplitude change is hereby a manifestation of the influence of the radial dependence function $A_{dbe}(r(\theta_b))$ on the resulting signal. Since the symmetric barrel case is being considered, i.e. $r(\theta_b)$=const, the radial function is constant and therefore imposes only scaling and no distortion of the angular Gaussian function.

Following is an analytical formula for a simplified approximation of the radial dependence function, by considering a degenerate ID case of X-ray propagation followed by Compton backscattering or generation of XRF.

Consider a ray of photons at energy $E_0$ and original intensity $I_0$ propagating in x direction through non-uniform absorbing medium, whose attenuation coefficient at energy $E_0$ is given by the function $\mu_{E_0}(x)$. The beam can be assumed infinitesimally narrow, and we seek to estimate the number of photons backscattered to the beam origin from the medium.

In accordance to the Beer-Lambert law, the number of photons arriving at point y—is given by:

$$I_{trans}(y) = I_0 e^{-\int_0^y \mu^{E_0}(x)dx} \quad (4)$$

By definition of the attenuation coefficient, the following number of photons will be scattered locally at point y through Compton scattering:

$$I_{absorbed}^{CMT}(y) = \mu_{CMT}^{E_0}(y) \cdot I_0 e^{-\int_0^y \mu^{E_0}(x)dx} \quad (5)$$

Where $\mu_{CMT}^{E_0}(x)$ is the Compton component of the attenuation coefficient $\mu_{E_0}(x)$. Part of those photons are backscattered in the direction opposite to the direction of propagation, their portion being defined by a linear factor $\tau_{CMT}^{E_0}$, and their energy, $E_{CMT}$, determined by the Klein-Nishina formula. The backscattered ray of photons undergoes absorption while propagating in the backward direction towards the origin of the beam. The number of photons returning from point y to the point of origin is then:

$$I_{returned}^{CMT}(y) = \tau_{CMT}^{E_0} \cdot \mu_{CMT}^{E_0}(y) \cdot I_0 e^{-\int_0^y (\mu^{E_0}(x) + \mu^{E_{CMT}}(x))dx} \quad (6)$$

In order to determine the overall number of backscattered photons, integrate (6) over y and obtain:

$$I_{returned}^{CMT} = \tau_{CMT}^{E_0} \cdot I_0 \cdot \int_0^\infty \mu_{CMT}^{E_0}(y) \cdot e^{-\int_0^y (\mu^{E_0}(x) + \mu^{E_{CMT}}(x))dx} dy \quad (7)$$

Recalling the assumption that the radial direction comprises only two types of materials—iodinated colon contents and soft tissue, all attenuation functions of the form $\mu^E(x)$ can be replaced with a step function $$u^E(x) = \begin{cases} \mu^E(m_1) & \text{for } x < r \\ \mu^E(m_2) & \text{for } x \geq r \end{cases} \quad (8)$$

where r is the distance to colon-wall, and m1 and m2 correspond to iodinated colon-contents and surrounding soft tissue respectively. Using (8), the integrals from equation (7) can be solved analytically, resulting in (9):

$$I_{returned}^{CMT} = \tau_{CMT}^{E_0} \cdot I_0 \cdot \left( e^{-(\mu^{E_0}(m_1) + \mu^{E_{CMT}}(m_1))r} \cdot \right.$$

$$\left( \frac{\mu_{CMT}^{E_0}(m_2)}{\mu^{E_0}(m_2) + \mu^{E_{CMT}}(m_2)} - \frac{\mu_{CMT}^{E_0}(m_1)}{\mu^{E_0}(m_1) + \mu^{E_{CMT}}(m_1)} \right) +$$

$$\left. \frac{\mu_{CMT}^{E_0}(m_1)}{\mu^{E_0}(m_1) + \mu^{E_{CMT}}(m_1)} \right) \quad (9)$$

Equation (9) can be reformulated as an exponential expression of the form:

$$I_{returned}^{CMT} = (C_3^{CMT} - C_2^{CMT}) \cdot \exp(-C_1^{CMT} \cdot r) + C_2^{CMT} \quad (10)$$

Where $C_1^{CMT}$, $C_2^{CMT}$ and $C_3^{CMT}$ are positive constant coefficients and r is the distance to the colon wall.

By analogy one can perform similar derivation for the estimated returned XRF signal:

$$I_{returned}^{XRF} = \tau_{XRF}^{E_0} \cdot I_0 \cdot \left( e^{-(\mu^{E_0}(m_1) + \mu^{E_{XRF}}(m_1))r} \cdot \right. \quad (11)$$

$$\left( \frac{\mu_{Photo}^{E_0}(m_2)}{\mu^{E_0}(m_2) + \mu^{E_{XRF}}(m_2)} - \frac{\mu_{Photo}^{E_0}(m_1)}{\mu^{E_0}(m_1) + \mu^{E_{XRF}}(m_1)} \right) +$$

$$\left. \frac{\mu_{Photo}^{E_0}(m_1)}{\mu^{E_0}(m_1) + \mu^{E_{XRF}}(m_1)} \right)$$

Where Photo corresponds to photoelectric absorption process, and $E_{XRF}$ is the energy of the XRF radiation of Iodine. Since in this case, the material $m_2$ corresponds to the out-of-colon soft tissue where there is no Iodine present, we may substitute $\mu_{Photo}^{E_0}(m_2)=0$, so equation (1) can be reformulated as:

$$I_{returned}^{XRF} = (1 - C_2^{XRF}) \cdot \exp(-C_1^{XRF} \cdot r) \quad (12)$$

The trends yielded by equations (10) and (12) are fully aligned with the trends exhibited in the corresponding curves of FIG. 7, confirming that (10) and (12) constitute a good approximation for the radial dependence function.

Formulation of the Combined Forward Gaussian Model:

Incorporating findings from the above explanations into equation (3) yields capsule detector readings as a function of the beam angular position α:

$$R_{dba} = \sum_{b=1}^{3} A_{dbe}(r(\alpha + \theta_b)) \cdot e^{-\frac{(\alpha + \theta_b - \theta_d)^2}{2\sigma_{dbe}^2}} \quad (13)$$

$$A_{dbe}(r) = (C_3^{dbe} - C_2^{dbe}) \cdot \exp(-C_1^{dbe} \cdot r) + C_2^{dbe}$$

Where $\theta_b$ and $\theta_d$ are the constant relative angles of the beams and detectors within the capsule assembly (for simplicity one can set $\theta_{b=1} = \theta_{d=1} = 0°$). Coefficients of the radial dependence function $C_i^{dbe}$ and the sigma of the Gaussian function $\sigma_{dbe}$ can be either obtained analytically or determined through the calibration process.

Optionally, the forward model formulated in equation (13) can serve as the core of an iterative reconstruction algorithm.

Figure 9:
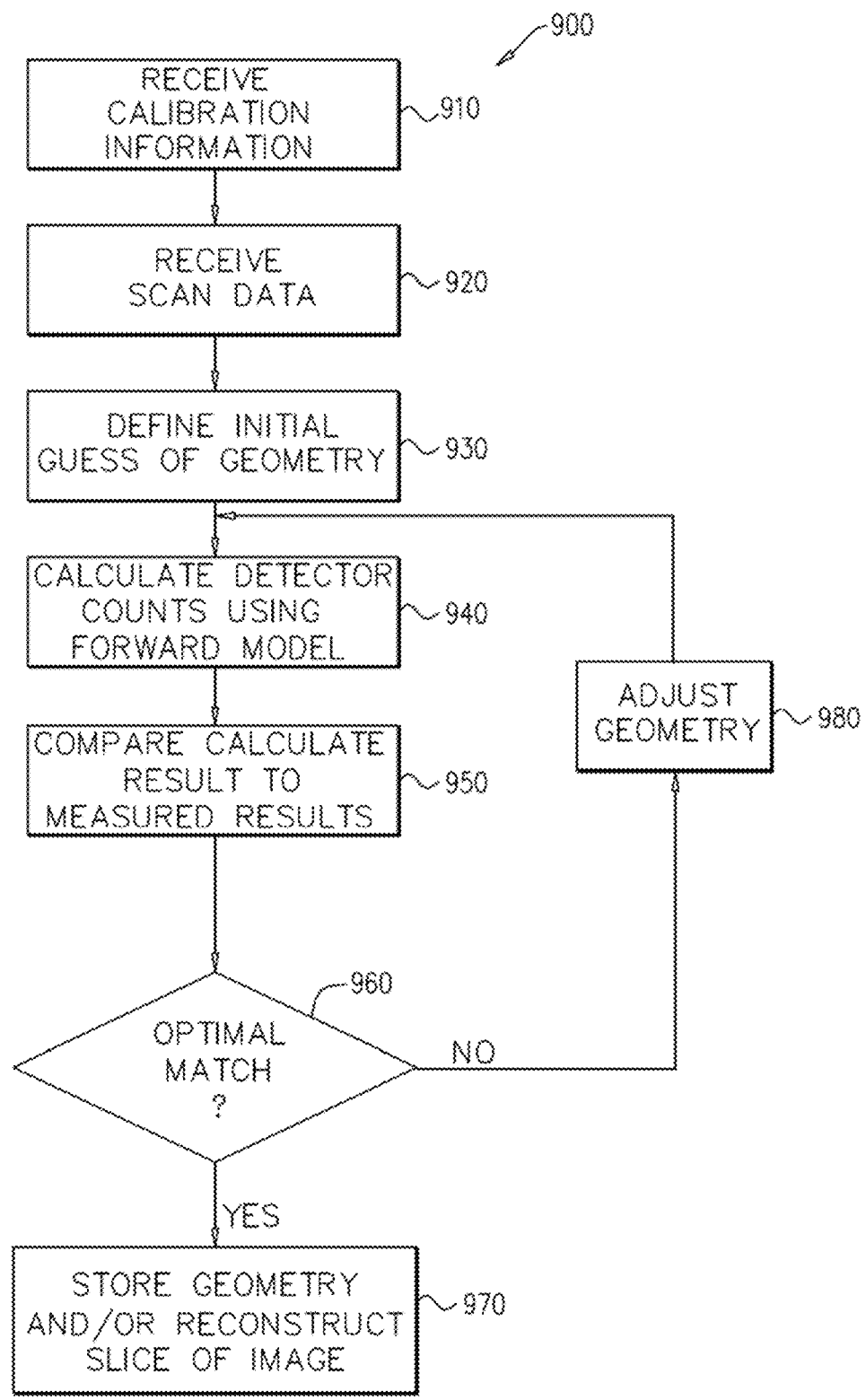
FIG. 9 is a flow diagram of a method of reconstructing an image of a colon, according to an exemplary embodiment of the disclosure.

Reconstruction Based on Forward Model:

FIG. 9 is a flow diagram of a method of reconstructing an image of a colon, according to an exemplary embodiment of the disclosure. In an exemplary embodiment of the disclosure, imaging capsule 150 traverses the gastrointestinal tract and scans the internal walls. During the trip through the gastrointestinal tract the imaging capsule 150 transmits the scanned data to the external receiver 120. Optionally, the external receiver 120 may communicate the data directly to computer 130 while the imaging capsule 150 is still inside patient 170 or after imaging capsule 150 exits from the patient 170 and ceases to transmit.

In an exemplary embodiment of the disclosure, external receiver 120 may be connected to computer 130, for example by BlueTooth, Wi-Fi, Ethernet, USB or any other type of connection. Alternatively, the scanned data may be stored on a memory card and physically transferred to computer 130 for analysis.

In an exemplary embodiment of the disclosure, before using each capsule the radiation source 115 and detectors 105 are tested, for example with a phantom well defined shaped system, for example as described above regarding FIG. 7 to determine the coefficients for each detector 105 and/or the entire system, which are used in the calculations. Optionally, the calibration information is provided (910) to computer 130 with or prior to receiving (920) the scan data.

In an exemplary embodiment of the disclosure, an initial guess of a geometry r(θ) of a contour of the colon (e.g. radius from the imaging capsule to the inner walls of the colon as a function of the angle around the imaging capsule) of a first slice of the colon 110 is defined (930) for starting the calculation process, for example it may be assumed that the first slice is a specific shape, e.g. a circle with a specific radius or an ellipse with specific focal points. Likewise the initial geometry of subsequent slices may be assumed to be based on the final optimal shape of a preceding slice.

Once a geometry r(θ) is defined program 145 on computer 130 calculates (940) expected detector counts using a forward model (e.g. the piecewise forward model or the Gaussian forward model as described above).

The calculated results are then compared (950) to the measured results (detector readings) that were received from the imaging capsule 150 at the same position in the colon 110. Optionally, the results are compared using an objective error function, such as least squares or maximum likelihood. In an exemplary embodiment of the disclosure, if the calculated results optimally match (960) the measured results (e.g. with a difference smaller than a preselected threshold value) then the geometry r(θ) is assumed to be correct and the geometry r(θ) can be used to represent a slice of the colon 110 at the specific position. Optionally, geometry r(θ) can be any shape, for example representing a contour with polyps and other abnormalities.

Figure 10B:
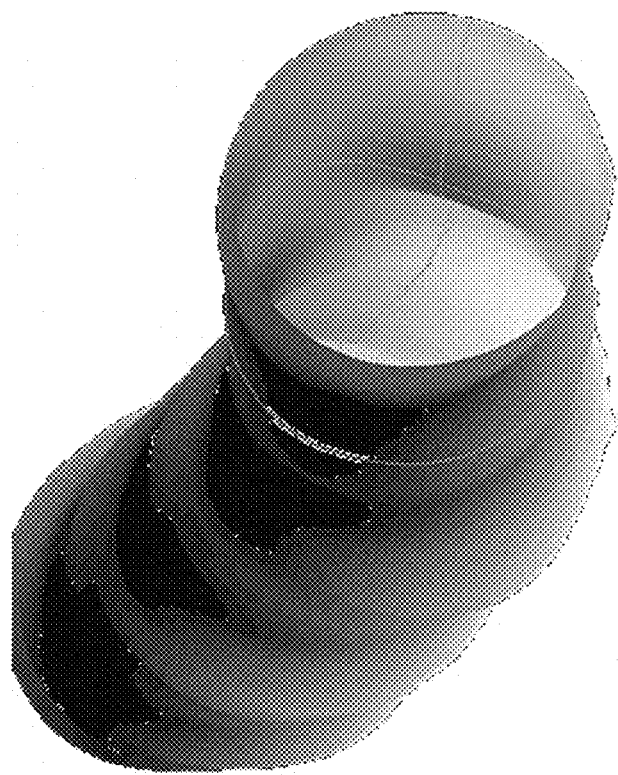
FIG. 10A-B are schematic illustrations of reconstructions of a colon, wherein A represents the reconstruction in 2D and B represents a 3D reconstruction, according to an exemplary embodiment of the disclosure.
Figure 10A:
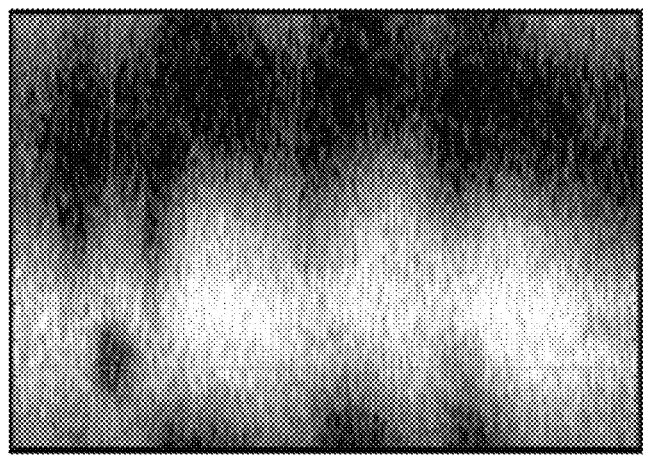

In an exemplary embodiment of the disclosure, once an optimal geometry r(θ) is achieved computer 130 can then use the geometry r(θ) to reconstruct (970) a slice of the image of the colon 110 and display it to the user or store the information for later use. Once program 145 determines the geometry of a sequential collection of slices, the program can combine them together and display a segment of the colon 110 or the entire colon 100. Optionally, computer 130 can display the colon to a practitioner and enable the practitioner to fly through the reconstructed image and/or zoom in or out to view specific areas of the colon. In some embodiments of the disclosure, the reconstructed representation may be a two dimensional waterfall image or a three dimensional image, for example as shown in FIG. 10 A and FIG. 10 B. The x-axis of the 2D image represents the angle relative to the capsule, while the y-axis is a simple index, equivalent to acquisition time. The color coding/shading in the 2D image reflects the reconstructed distances of the colon wall from the capsule ranges from dark to light. Accordingly, the dark localized regions seen in the reconstruction image shown in FIG. 10A, are the regions where the capsule has detected intrusions, relative to the colon wall, that may be interpreted as polyps.

In an exemplary embodiment of the disclosure, the reconstructed images may be aided by other positioning information acquired from imaging capsule 150, for example external recorder 120 may store the scan data with positioning data acquired from other sensors (e.g. accelerometers, coils, gyroscopes etc.) that keep track of position/motion of the imaging capsule 150.

In an exemplary embodiment of the disclosure, if the calculated data is not close enough then program 145 adjusts (980) the geometry r(θ) based on the counts and iteratively repeats the calculations by returning to (940) to recalculate detector counts. Optionally, the geometry near each detector 105 is adjusted based on the actual XRF count and CMT count relative to the calculated count, which as explained above indicate if the colon radius in the vicinity of the detector should be larger or smaller.

In some embodiment of the disclosure, program 145 is stored on a non-volatile computer storage medium (e.g. CD, DVD, USB drive) to be transferred to computers to analyze scan data and reconstruct images of a colon or a segment of a colon.

It should be appreciated that the above described methods and apparatus may be varied in many ways, including omitting or adding steps, changing the order of steps and the type of devices used. It should be appreciated that different features may be combined in different ways. In particular, not all the features shown above in a particular embodiment are necessary in every embodiment of the disclosure. Further combinations of the above features are also considered to be within the scope of some embodiments of the disclosure.

It will be appreciated by persons skilled in the art that the present disclosure is not limited to what has been particularly shown and described hereinabove.

We claim:

1. A method of reconstructing an image of a colon, comprising:
receiving scan data of a colon taken by an imaging capsule that traverses the colon from the inside; wherein said imaging capsule emits X-ray radiation inside the colon and includes detectors that detect photons that are returned toward the imaging capsule from X-ray fluorescence interactions and Compton back scattering interactions responsive to the X-ray radiation; and wherein the scan data includes counts of photons detected by each detector from X-ray fluorescence interactions and Compton back scattering interactions;
defining an initial guess of a geometry of a contour of a slice of the colon;
calculating count values for each detector responsive to the defined geometry using a forward model;
comparing the calculated count values of each detector with the values from the scan data;
if the results of the comparison do not indicate reaching an optimal match then adjust the defined geometry and repeat the calculating and comparing;
otherwise if an optimal match is achieved store the geometry to represent the slice.

2. The method according to claim 1, wherein the imaging capsule is first tested to determine calibration values required for performing said calculating.

3. The method according to claim 1, wherein the initial guess of the geometry of a slice of the colon is a specific shape.

4. The method according to claim 1, wherein the initial guess of the geometry of a slice of the colon is determined from a previously determined geometry of an adjacent slice of the colon.

5. The method according to claim 1, wherein the forward model encapsulates all physics processes necessary to estimate the count of each detector.

6. The method according to claim 1, wherein the forward model is a piecewise forward model that estimates the count of each detector based on the emitted radiation and an estimated response by each voxel of a space surrounding the imaging capsule.

7. The method according to claim 1, wherein the forward model is a Gaussian forward model that estimates the count of each detector based on the relative angular distance between each emitting beam and each detector, and the distance of the capsule center from the contour of the colon.

8. The method according to claim 1, wherein the optimal match is determined by using least means square or maximum likelihood to determine whether the results of the comparing have a difference less than a preselected threshold value.

9. The method according to claim 1, wherein the scan data includes position information of the imaging capsule in the colon with the detector counts, wherein the position information is determined independently of the detector counts.

10. The method according to claim 1, wherein the scan data includes a plurality of measurements comprising sets of detector counts and rotation angles of a radiation source for each position in the colon.

11. The method according to claim 1, wherein the scan data includes detector counts of a scan of an entire circumference of each position in the colon.

12. The method according to claim 1, wherein adjusting the defined geometry includes increasing a distance from the imaging capsule to the colon contour for specific rotation angles of a radiation source and decreasing the distance from the imaging capsule to the colon contour for other rotation angles.

13. A system for reconstructing an image of a colon, comprising:
    a computer or dedicated programmable computing hardware, configured to receive scan data of a colon taken by an imaging capsule that traverses the colon from the inside; wherein said imaging capsule emits X-ray radiation inside the colon and includes detectors that detect photons that are returned toward the imaging capsule from X-ray fluorescence interactions and Compton back scattering interactions responsive to the X-ray radiation; and wherein the scan data includes counts of photons detected by each detector from X-ray fluorescence interactions and Compton back scattering interactions;
    a computer program configured to be executed on the computer or dedicated programmable computing hardware and perform the following:
    defining an initial guess of a geometry of a contour of a slice of the colon;
    calculating count values for each detector responsive to the defined geometry using a forward model;
    comparing the calculated count values of each detector with the values from the scan data;
    if the results of the comparison do not indicate reaching an optimal match then adjust the defined geometry and repeat the calculating and comparing;
    otherwise if an optimal match is achieved store the geometry to represent the slice of the colon.

14. The system according to claim 13 wherein the forward model encapsulates all physics processes necessary to estimate the count of each detector.

15. The system according to claim 13, wherein the forward model is a piecewise forward model that estimates the count of each detector based on the emitted radiation and an estimated response by each voxel of a space surrounding the imaging capsule.

16. The system according to claim 13, wherein the forward model is a Gaussian forward model that estimates the count of each detector based on the relative angular distance between each emitting beam and each detector, and the distance of the capsule center from the contour of the colon.

17. The system according to claim 13, wherein the optimal match is determined by using least means square or maximum likelihood to determine if the results of the comparing have a difference less than a preselected threshold value.

18. The system according to claim 13, wherein the scan data includes position information of the imaging capsule in the colon with the detector counts, wherein the position information is determined independently of the detector counts.

19. The system according to claim 13, wherein the scan data includes a plurality of measurements comprising sets of detector counts and rotation angles of a radiation source for each position in the colon.

20. A non-volatile computer storage medium for storing a program to execute the method of claim 1.

* * * * *